United States Patent
Chaturvedi (10) Patent No.: US 11,992,338 B2
(45) Date of Patent: May 28, 2024

(54) SYSTEM AND METHOD USED TO DETECT OR DIFFERENTIATE TISSUE OR AN ARTIFACT

(71) Applicant: Briteseed, LLC, Chicago, IL (US)

(72) Inventor: Amal Chaturvedi, San Jose, CA (US)

(73) Assignee: Briteseed, LLC, Chicago, IL (US)

( * ) Notice: Subject to any disclaimer, the term of this patent is extended or adjusted under 35 U.S.C. 154(b) by 472 days.

(21) Appl. No.: 17/417,746

(22) PCT Filed: Dec. 27, 2019

(86) PCT No.: PCT/US2019/068841
§ 371 (c)(1),
(2) Date: Jun. 23, 2021

(87) PCT Pub. No.: WO2020/142394
PCT Pub. Date: Jul. 9, 2020

(65) Prior Publication Data
US 2022/0287628 A1    Sep. 15, 2022

Related U.S. Application Data

(60) Provisional application No. 62/786,532, filed on Dec. 30, 2018.

(51) Int. Cl.
*A61B 5/00* (2006.01)
*A61B 5/107* (2006.01)

(52) U.S. Cl.
CPC ............ *A61B 5/489* (2013.01); *A61B 5/1079* (2013.01); *A61B 5/6847* (2013.01);
(Continued)

(58) Field of Classification Search
CPC ..... A61B 5/489; A61B 5/1079; A61B 5/6847; A61B 5/7239; A61B 5/725;
(Continued)

(56) References Cited

U.S. PATENT DOCUMENTS

| 4,833,418 A | 5/1989 | Quintus et al. |
| 5,129,400 A | 7/1992 | Makino et al. |

(Continued)

FOREIGN PATENT DOCUMENTS

| EP | 2 353 534 | 8/2011 |
| GB | 1 445 678 | 8/1976 |

(Continued)

OTHER PUBLICATIONS

Akl et al., Performance Assessment of an Opto-Fluidic Phantom Mimicking Porcine Liver Parenchyma, J. Bio. Optics, vol. 17(7) 077008-1 to 077008-9 (Jul. 2012).

(Continued)

*Primary Examiner* — Scott M. Getzow
(74) *Attorney, Agent, or Firm* — Cook Alex Ltd.

(57) ABSTRACT

A surgical system includes at least one light emitter and an array of light sensors disposed at the working end of the surgical instrument, individual light sensors in the array of light sensors adapted to generate a signal comprising a non-pulsatile component. The system also includes a controller coupled to the array of light sensors, the controller including an analyzer configured to determine a curve of the non-pulsatile components of the signals of each of the individual light sensors in the array of light sensors, smooth the curve, calculate a derivative of the smoothed curve; invert the smoothed curve, calculate a derivative of the inverted smoothed curve, take a difference between the derivatives, smooth the resultant curve, estimate zero crossings of the smoothed, resultant curve, apply a signum function to points adjacent each zero crossing, if any, and identify a region of interest, if any, based on the result.

8 Claims, 5 Drawing Sheets

(52) U.S. Cl.
CPC ............ *A61B 5/7239* (2013.01); *A61B 5/725* (2013.01); *A61B 2505/05* (2013.01); *A61B 2562/0238* (2013.01); *A61B 2562/043* (2013.01)

(58) Field of Classification Search
CPC ........ A61B 2505/05; A61B 2562/0238; A61B 2562/043; A61B 5/4836; A61B 5/1459
See application file for complete search history.

(56) References Cited

U.S. PATENT DOCUMENTS

| | | |
|---|---|---|
| 5,259,761 A | 11/1993 | Schnettler et al. |
| 5,762,609 A | 6/1998 | Benaron et al. |
| 5,769,791 A | 6/1998 | Benaron et al. |
| 5,772,597 A | 6/1998 | Goldberger et al. |
| 5,785,658 A | 7/1998 | Benaron et al. |
| 5,807,261 A | 9/1998 | Benaron et al. |
| 5,987,346 A | 11/1999 | Benaron et al. |
| 6,178,340 B1 | 1/2001 | Svetliza |
| 6,341,172 B1 | 1/2002 | Xu et al. |
| 6,374,128 B1 | 4/2002 | Toida et al. |
| 6,569,104 B2 | 5/2003 | Ono et al. |
| 6,594,518 B1 | 7/2003 | Benaron et al. |
| 6,922,577 B2 | 7/2005 | Nakashima et al. |
| 7,006,861 B2 | 2/2006 | Flock et al. |
| 7,112,201 B2 | 9/2006 | Truckai et al. |
| 7,235,072 B2 | 6/2007 | Sartor et al. |
| 7,515,265 B2 | 4/2009 | Alfano et al. |
| 7,740,591 B1 | 6/2010 | Starr et al. |
| 7,749,217 B2 | 7/2010 | Podhajsky |
| 7,904,138 B2 | 3/2011 | Goldman et al. |
| 7,983,738 B2 | 7/2011 | Goldman et al. |
| 8,058,771 B2 | 11/2011 | Giordano et al. |
| 8,073,531 B2 | 12/2011 | Goldman et al. |
| 8,118,206 B2 | 2/2012 | Zand et al. |
| 8,123,745 B2 | 2/2012 | Beeckler et al. |
| 8,150,500 B2 | 4/2012 | Goldman et al. |
| 8,244,333 B2 | 8/2012 | Wood et al. |
| 8,255,040 B2 | 8/2012 | Goldman et al. |
| 8,295,904 B2 | 10/2012 | Goldman et al. |
| 8,380,291 B2 | 2/2013 | Wood et al. |
| 8,391,960 B2 | 3/2013 | Wood et al. |
| 8,417,306 B2 | 4/2013 | Cheng |
| 8,463,364 B2 | 6/2013 | Wood et al. |
| 8,467,857 B2 | 6/2013 | Kim et al. |
| 8,478,386 B2 | 7/2013 | Goldman et al. |
| 8,483,805 B2 | 7/2013 | Takenoshita et al. |
| 8,483,819 B2 | 7/2013 | Choi et al. |
| 8,489,178 B2 | 7/2013 | Wood et al. |
| 8,586,924 B2 | 11/2013 | Demos |
| 8,649,568 B2 | 2/2014 | Sato |
| 8,649,848 B2 | 2/2014 | Crane et al. |
| 8,682,418 B2 | 3/2014 | Tanaka |
| 8,706,200 B2 | 4/2014 | Goldman et al. |
| 8,712,498 B2 | 4/2014 | Goldman et al. |
| 8,750,970 B2 | 6/2014 | Goldman et al. |
| 8,792,967 B2 | 7/2014 | Sato |
| 8,818,493 B2 | 8/2014 | Goldman et al. |
| 8,838,210 B2 | 9/2014 | Wood et al. |
| 9,526,921 B2 | 12/2016 | Kimball et al. |
| 2002/0169381 A1 | 11/2002 | Asada et al. |
| 2003/0036685 A1 | 2/2003 | Goodman |
| 2003/0036751 A1 | 2/2003 | Anderson et al. |
| 2003/0120306 A1 | 6/2003 | Burbank et al. |
| 2004/0111085 A1 | 6/2004 | Singh |
| 2005/0143662 A1 | 6/2005 | Marchitto et al. |
| 2005/0180620 A1 | 8/2005 | Takiguchi |
| 2006/0020212 A1 | 1/2006 | Xu et al. |
| 2006/0052850 A1 | 3/2006 | Darmos et al. |
| 2006/0100523 A1 | 5/2006 | Ogle et al. |
| 2006/0155194 A1 | 7/2006 | Marcotte et al. |
| 2007/0038118 A1 | 2/2007 | DePue et al. |
| 2009/0018414 A1 | 1/2009 | Toofan |
| 2009/0054908 A1 | 2/2009 | Zand et al. |
| 2010/0222786 A1 | 9/2010 | Kassab |
| 2010/0249763 A1 | 9/2010 | Larson et al. |
| 2011/0021925 A1 | 1/2011 | Wood et al. |
| 2011/0245685 A1 | 10/2011 | Murata et al. |
| 2012/0016362 A1 | 1/2012 | Heinrich et al. |
| 2012/0046555 A1 | 2/2012 | Takamatsu et al. |
| 2012/0143182 A1 | 6/2012 | Ullrich et al. |
| 2012/0172842 A1 | 7/2012 | Sela et al. |
| 2012/0296205 A1 | 11/2012 | Chernov et al. |
| 2013/0102905 A1 | 4/2013 | Goldman et al. |
| 2013/0226013 A1 | 8/2013 | McEwen et al. |
| 2013/0267874 A1 | 10/2013 | Marcotte et al. |
| 2014/0086459 A1 | 3/2014 | Pan et al. |
| 2014/0100455 A1 | 4/2014 | Goldman et al. |
| 2014/0155753 A1 | 6/2014 | McGuire, Jr. et al. |
| 2014/0194751 A1 | 7/2014 | Goldman et al. |
| 2014/0236019 A1 | 8/2014 | Rahum |
| 2014/0276088 A1 | 9/2014 | Drucker |
| 2014/0313482 A1 | 10/2014 | Shahidi et al. |
| 2015/0011896 A1 | 1/2015 | Yelin et al. |
| 2015/0051460 A1 | 2/2015 | Saxena et al. |
| 2015/0066000 A1 | 3/2015 | An et al. |
| 2016/0235368 A1 | 8/2016 | Akkermans |
| 2017/0181701 A1 | 6/2017 | Fehrenbacher et al. |
| 2017/0311877 A1 | 11/2017 | Watanabe et al. |
| 2017/0367772 A1 | 12/2017 | Gunn et al. |
| 2018/0042522 A1 | 2/2018 | Subramanian et al. |
| 2018/0098705 A1 | 4/2018 | Chaturvedi et al. |
| 2018/0289315 A1 | 10/2018 | Chaturvedi et al. |
| 2018/0317999 A1 | 11/2018 | Park et al. |
| 2019/0038136 A1 | 2/2019 | Gunn et al. |
| 2019/0046220 A1 | 2/2019 | Chaturvedi et al. |
| 2019/0175158 A1 | 6/2019 | Chaturvedi et al. |
| 2020/0268311 A1 | 8/2020 | Shukair et al. |
| 2020/0337633 A1 | 10/2020 | Chaturvedi et al. |
| 2020/0345297 A1 | 11/2020 | Chaturvedi et al. |
| 2021/0068856 A1 | 3/2021 | Gunn et al. |

FOREIGN PATENT DOCUMENTS

| | | |
|---|---|---|
| JP | H02-177706 | 7/1990 |
| JP | H10-005245 | 1/1998 |
| JP | H10-234715 | 9/1998 |
| JP | 2002-000576 | 1/2002 |
| JP | 2002-051983 | 2/2002 |
| JP | 2003-019116 | 1/2003 |
| JP | 2010-081972 | 4/2010 |
| JP | 2016-531629 | 10/2016 |
| JP | 2018-534054 | 11/2018 |
| WO | WO98/27865 | 7/1998 |
| WO | WO2001/060427 | 8/2001 |
| WO | WO2003/039326 | 5/2003 |
| WO | WO2004/030527 | 4/2004 |
| WO | WO2005/091978 | 10/2005 |
| WO | WO2008/082992 | 7/2008 |
| WO | WO2009/144653 | 12/2009 |
| WO | WO2011/013132 | 2/2011 |
| WO | WO2012/158774 | 11/2012 |
| WO | WO2013/134411 | 9/2013 |
| WO | WO2014/194317 | 12/2014 |
| WO | WO2015/148504 | 10/2015 |
| WO | WO2016/117106 | 7/2016 |
| WO | WO2016/134327 | 8/2016 |
| WO | WO2016/134330 | 8/2016 |
| WO | WO 2017/062720 | 4/2017 |
| WO | WO 2017/139624 | 8/2017 |
| WO | WO2017/139642 | 8/2017 |
| WO | WO 2018/044722 | 3/2018 |
| WO | WO2019/050928 | 3/2019 |
| WO | WO2019/126633 | 6/2019 |
| WO | WO2019/143965 | 7/2019 |
| WO | WO2020/041203 | 2/2020 |

OTHER PUBLICATIONS

Comtois et al., A Comparative Evaluation of Adaptive Noise Cancellation Algorithms for Minimizing Motion Artifacts in a (56) References Cited

OTHER PUBLICATIONS

Forehead-Mounted Wearable Pulse Oximeter, Conf. Proc. IEEE Eng. Med. Biol. Soc., 1528-31 (2007).

Figueiras et al., Self-Mixing Microprobe for Monitoring Microvascular Perfusion in Rat Brain, Med. Bio. Eng'r Computing 51:103-112 (Oct. 12, 2012).

Hammer et al., A Simple Algorithm for In Vivo Ocular Fundus Oximetry Compensating for Non-Haemoglobin Absorption and Scattering, Phys. Med. Bio. vol. 47, N233-N238 (Aug. 21, 2002).

Ibey et al., Processing of Pulse Oximeter Signals Using Adaptive Filtering and Autocorrelation to Isolate Perfusion and Oxygenation Components, Proc SPIE, vol. 5702, 54-60 (2005).

Li et al., Pulsation-Resolved Deep Tissue Dynamics Measured with Diffusing-Wave Spectroscopy, Optics Express, vol. 14, No. 17, 7841-7851 (Aug. 21, 2006).

Mendelson et al., In-vitro Evaluation of a Dual Oxygen Saturation/Hematocrit Intravascular Fiberoptic Catheter, Biomed Instrum. Technol. 24(3):199-206 (May/Jun. 1990).

Phelps et al., Rapid Ratiometric Determination of Hemoglobin Concentration using UV-VIS Diffuse Reflectance at Isobestic Wavelengths, Optics Express, vol. 18, No. 18, 18779-18792 (Aug. 30, 2010).

Subramanian, Real Time Perfusion and Oxygenation Monitoring in an Implantable Optical Sensor, Thesis Texas A&M Univ. (Dec. 2004).

Subramanian, Real-Time Separation of Perfusion and Oxygenation Signals for an Implantable Sensor Using Adaptive Filtering, IEEE Trans. Bio. Eng'g, vol. 52, No. 12, 2016-2023 (Dec. 2005).

Subramanian, An Autocorrelation-Based Time Domain Analysis Technique for Monitoring Perfusion and Oxygenation in Transplanted Organs, IEEE Trans. Bio. Eng'g, vol. 52, No. 7, 1355-1358 (Jul. 2005).

International Search Report and Written Opinion, counterpart PCT application PCT/US2019/068841, 15 pages (dated Mar. 16, 2020).

Chaturvedi, Amal et al., "Blood vessel detection, localization and estimation using a smart laparoscopic grasper: a Monte Carlo study" vol. 9, No. 5 (Apr. 3, 2018) (14 pages).

Pu, Dong-Mel et al., "First and second order full-differential in the edge detection of images", 2013 International Conference on Machine Learning and Cybernetics, IEEE, vol. 4, pp. 1543-1547, (Jul. 14, 2013).

Abramowitz, Milton et al., "Handbook of Mathematical Functions", Sections 25.2 and 25.3.4, pp. 878, 883 (Jun. 1, 1964).

Notice of Reasons for Refusal and English-language machine translation, counterpart Japanese application No. 2021-538310 (dated Sep. 5, 2023) (10 pages).

Search Report and English-language machine translation, counterpart Japanese App. No. 2021-538310 (dated Aug. 4, 2023) (25 pages).

SYSTEM AND METHOD USED TO DETECT OR DIFFERENTIATE TISSUE OR AN ARTIFACT

The present application is a U.S. National Stage of PCT International Patent Application No. PCT/US2019/068841, filed Dec. 27, 2019, which claims the benefit of U.S. Provisional Patent Application No. 62/786,532, filed Dec. 30, 2018, both of which are hereby incorporated herein by reference.

BACKGROUND

This patent is directed to a system and method used to detect or differentiate tissue or an artifact, such as a vessel, and in particular to a system and method used to detect or differentiate tissue or an artifact, where the system includes at least one light emitter and at least one light sensor disposed at a distal end of a shaft.

Systems and methods that identify artifacts, and in particular vessels, in the surgical field during a surgical procedure provide valuable information to the surgeon or surgical team. U.S. hospitals lose billions of dollars annually in unreimbursable costs because of inadvertent vascular damage during surgery. In addition, the involved patients face a mortality rate of up to 32%, and likely will require corrective procedures and remain in the hospital for an additional nine days, resulting in tens, if not hundreds, of thousands of dollars in added costs of care. Consequently, there is significant value to be obtained from methods and systems that permit accurate determination of the presence of vessels, such as blood vessels, in the surgical field, such that these costs may be reduced or avoided.

Systems and methods that provide information regarding the presence of blood vessels in the surgical field are particularly important during minimally invasive surgical procedures. Traditionally, surgeons have relied upon tactile sensation during surgical procedures both to identify blood vessels and to avoid inadvertent damage to these vessels. Because of the shift towards minimally invasive procedures, including laparoscopic and robotic surgeries, surgeons have lost the ability to use direct visualization and the sense of touch to make determinations as to the presence of blood vessels in the surgical field. Consequently, surgeons must make the determination whether blood vessels are present in the surgical field based primarily on convention and experience. Unfortunately, anatomical irregularities frequently occur because of congenital anomalies, scarring from prior surgeries, and body habitus (e.g., obesity). Systems and methods that would permit surgeons to determine the presence and/or the characteristics of vessels in the surgical field during surgery (potentially in real time or near real time) under such conditions would be a significant advantage.

On the other hand, while it would be advantageous to include systems and methods that provide information regarding the presence of blood vessels in the surgical field, the adoption of such systems and methods would be impeded if these systems and methods made the surgical procedure more complicated. Consequently, it is advantageous that the systems and methods do not involve significant thought on the part of the surgeon or surgical team in using the system or method for detecting or differentiating tissue or an artifact, like a vessel, or significant preparation of the surgical field or the patient for use of the system or method.

As set forth in more detail below, the present disclosure describes a user interface embodying advantageous alternatives to the existing systems and methods, which may provide for improved identification for avoidance or isolation of tissue or artifacts, such as vessels, without undue complication of the surgical instrument or surgical procedure.

SUMMARY

According to an aspect of the present disclosure, a surgical system includes a surgical instrument, at least one light emitter disposed at a working end of the surgical instrument, an array of light sensors disposed at the working end of the surgical instrument, individual light sensors in the array of light sensors adapted to generate a signal comprising a non-pulsatile component, and a controller coupled to the array of light sensors. The controller includes an analyzer configured to determine a curve of the non-pulsatile components of the signals of each of the individual light sensors in the array of light sensors, smooth the curve to generate a smoothed curve, calculate a derivative of the smoothed curve, invert the smoothed curve to generate an inverted smoothed curve, calculate a derivative of the inverted smoothed curve, take a difference between the derivative of the inverted smoothed curve and the derivative of the smoothed curve to generate a resultant curve, smooth the resultant curve to generate a smoothed, resultant curve, estimate zero crossings of the smoothed, resultant curve, apply a signum function to points adjacent each zero crossing, if any, to generate a result; and identify a region of interest, if any, based on the result for points adjacent each zero crossing, if any.

BRIEF DESCRIPTION OF THE DRAWINGS

The disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings is necessarily to scale.

DETAILED DESCRIPTION OF VARIOUS EMBODIMENTS

The embodiments described herein provide a system and method for detecting or differentiating regions of interest in a curve, which system and method also involve detecting or differentiating tissue or artifacts, such as vessels, and which system and method can be used with or in surgical systems or instruments. Such a system may include at least one light emitter disposed at a working end of the surgical instrument and an array of light sensors disposed at the working end of the surgical instrument, individual light sensors in the array of light sensors adapted to generate a signal comprising a non-pulsatile component. The system may also include a controller coupled to the array of light sensors, the controller including an analyzer. The analyzer is configured to determine a curve of the non-pulsatile components of the signals of each of the individual light sensors in the array of light sensors, smooth the curve to generate a smoothed curve, calculate a derivative of the smoothed curve, invert the smoothed curve to generate an inverted smoothed curve, calculate a derivative of the inverted smoothed curve, take a difference between the derivative of the inverted smoothed curve and the derivative of the smoothed curve to generate a resultant curve, smooth the resultant curve to generate a smoothed, resultant curve, estimate zero crossings of the smoothed, resultant curve, apply a signum function to points adjacent each zero crossing, if any, to generate a result, and identify a region of interest, if any, based on the result for points adjacent each zero crossing, if any.

Turning first to FIGS. 1-6, embodiments of such a surgical system 100 are illustrated, which system 100 may be used to determine, for example, a characteristic (e.g., presence, diameter, etc.) of a vessel, V, within a region 102 of tissue, T, proximate to a working end 104 of a surgical instrument 106. It will be understood that the vessel V may be connected to other vessels with the region 102 of tissue T, and in addition, the vessel V may extend beyond the region 102 so as to be in fluid communication with other organs (e.g., the heart) also found in the body of the patient. Furthermore, while the tissue T appears in FIGS. 1-4 to surround fully the vessel V (in terms of both circumference and length) to a particular depth, this need not be the case in all instances where the system 100 is used. For example, the tissue T may only partially surround the circumference of and/or only surround a section of the length of the vessel V, or the tissue T may overlie the vessel V in a very thin layer. As further non-limiting examples, the vessel V may be a blood vessel, and the tissue T may be connective tissue, adipose tissue and/or liver tissue.

According to the illustrated embodiments, the working end 104 of the surgical instrument 106 is also a distal end of a shaft 108. Consequently, the working end and the distal end will be referred to as working end 104 or distal end 104. The shaft 108 also has a proximal end 110, and a grip or handle 112 (referred to herein interchangeably as grip 112) is disposed at the proximal end 110 of the shaft 108. The grip 112 is designed in accordance with the nature of the instrument 106; as to the thermal ligation device illustrated in FIG. 1, the grip 112 may be a pistol-type grip including a trigger 114. As one alternative, finger rings arranged in a generally scissors-type grip may be used.

While the working or distal end 104 and the proximal end 110 with grip 112 are illustrated as disposed at opposite-most ends of the shaft 108, it will be recognized that certain surgical instruments have working ends (where a tool tip is attached, for example) disposed on the opposite-most ends of the shaft and a gripping region disposed intermediate to the opposite working ends. In accordance with the terms "distal" and "proximal" as used herein, the working ends of such an instrument are referred to herein as the distal ends and the gripping region as the proximal end. Relative to the illustrated embodiments, however, the distal and proximal ends are located at opposite-most (or simply opposite) ends of the shaft 108.

As mentioned above, according to the preferred embodiments illustrated, the surgical system 100 includes a sensor with at least one light emitter 120 (or simply the light emitter 120) and one or more light sensors or detectors 122 (or simply the light sensors 122). See FIGS. 2-4. According to the illustrated embodiments, a controller 124 is coupled to the light emitter 120 and the light sensors 122, which controller 124 may include a splitter 126 and an analyzer 128 as explained below. See FIG. 1.

Figure 2:
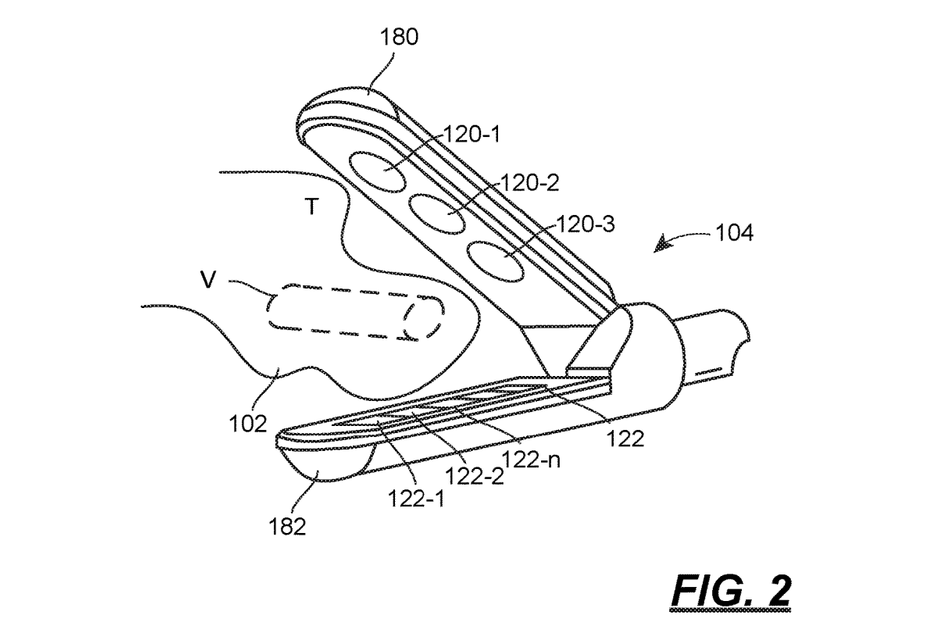
FIG. 2 is an enlarged, fragmentary view of a transmittance-based embodiment of the surgical instrument of FIG. 1 with light emitters and light sensors, and a section of a vessel illustrated as disposed between the light emitters and light sensors.
Figure 3:
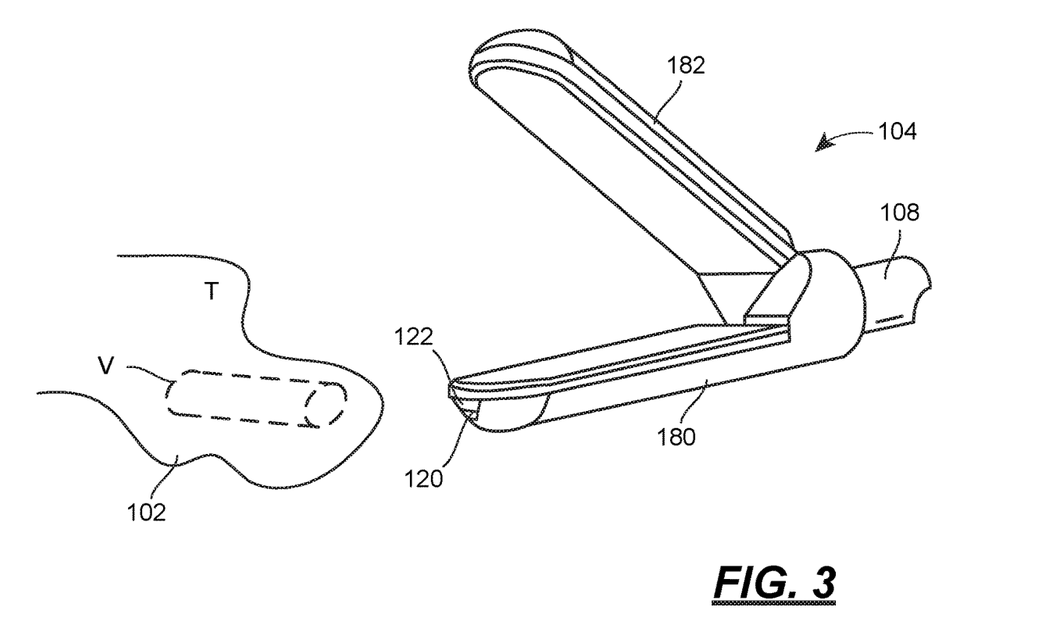
FIG. 3 is an enlarged, fragmentary view of an embodiment of the surgical instrument of FIG. 1 also fitted with a reflectance-based system with light emitter and light sensor with fixed spacing, and a section of an vessel illustrated as proximate the light emitter and light sensors.
Figure 4:
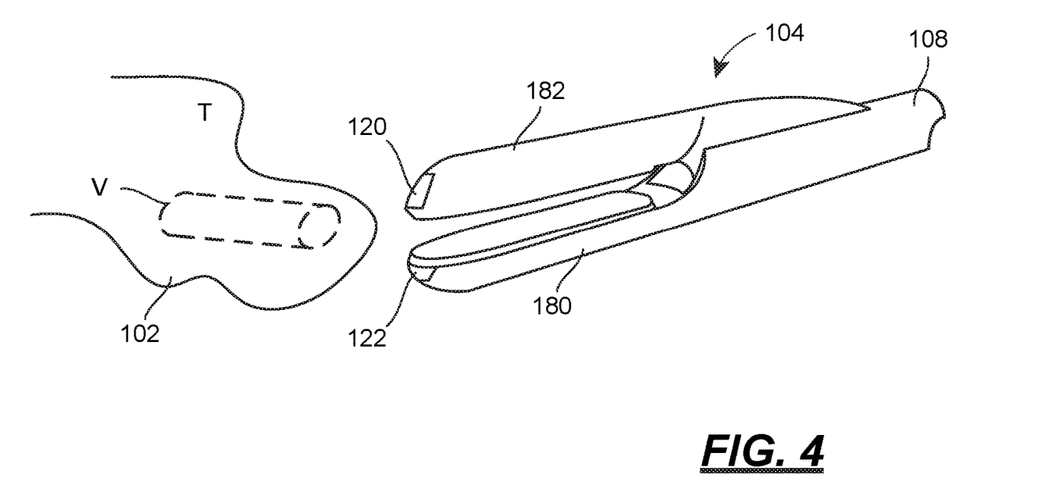
FIG. 4 is an enlarged, fragmentary view of another embodiment of a surgical instrument also fitted with a reflectance-based system with light emitter and light sensor having an adjustable spacing relative to each other, and a section of a vessel illustrated as proximate the light emitter and light sensor.

The light emitter 120 is disposed at the working end 104 of the surgical instrument 106. The light sensors 122 are also disposed at the working end 104 of the surgical instrument 106. In either case, the phrase "disposed at" may refer to the placement of the emitter 120 or sensor 122 physically at the working end 104, or placement of a fiber or other light guide at the working end 104, which light guide is coupled to the emitter 120 or sensor 122 which then may be placed elsewhere. The system 100 may operate according to a transmittance-based approach, such that the light sensors 122 are disposed opposite and facing the light emitter(s) 120, for example on opposite jaws of a surgical instrument 106 as illustrated in FIG. 2. In addition, the system 100 may include a reflectance-based system (for forward-facing vessel and/or tissue detection), such that the light emitter 120 and the light sensors 122 may face in a common direction and with fixed spacing therebetween, for example on a single jaw of a two jaw device (see FIG. 3). Alternatively, the light emitter 120 and the light sensor 122 of a reflectance-based system may be constructed such that the spacing between the light emitter 120 and the light sensor 122 may be adjusted, for example by positioning the light emitter 120 at the end or tip of one of the jaws of a two jaw device and the light sensor 122 at the end or tip of the other the jaws of the two jaw device (see FIG. 4). As to the operation of such reflectance-based systems, PCT Application No. PCT/US17/17436, filed Feb. 10, 2017, is incorporated herein by reference in its entirety.

The light emitter 120 may be configured to emit light of at least one wavelength. For example, the light emitter 120 may emit light having a wavelength of 660 nm. This may be achieved with a single element, or a plurality of elements (which elements may be arranged or configured into an array, for example, as explained in detail below). In a similar fashion, the light sensor 122 is configured to detect light at the at least one wavelength (e.g., 660 nm). According to the embodiments described herein, the light sensor 122 includes a plurality of elements, which elements are arranged or configured into an array.

According to certain embodiments, the light emitter 120 may be configured to emit light of at least two different wavelengths, and the light sensor 122 may be configured to detect light at the at least two different wavelengths. As one example, the light emitter 120 may emit and the light sensor 122 may detect light in the visible range and light in the near-infrared or infrared range. Specifically, the light emitter 120 may emit and the light sensor 122 may detect light at 660 nm and at 910 nm. Such an embodiment may be used, for example, to ensure optimal penetration of blood vessel V and the surrounding tissue T under in vivo conditions.

Depending upon the effect of changes in blood flow, light of a third wavelength may also be emitted and sensed. That is, if the method of detection is found to be sensitive to varying rates of blood flow in the vessel of interest, light at 810 nm (i.e., at the isobestic point) may be emitted and sensed to permit normalization of the results to limit or eliminate the effects of changes in blood flow rate. Additional wavelengths of light may also be used.

According to certain embodiments, each individual light sensor 122 is configured to generate a signal comprising a first pulsatile component and a second non-pulsatile component. It will be recognized that the first pulsatile component may be an alternating current (AC) component of the signal, while the second non-pulsatile component may be a direct current (DC) component. Where the light sensor 122 is in the form of an array, the pulsatile and non-pulsatile information may be generated for each element of the array, or at least for each element of the array that defines at least one row of the array.

As to the pulsatile component, it will be recognized that a blood vessel may be described as having a characteristic pulsation of approximately 60 pulses (or beats) per minute. While this may vary with the patient's age and condition, the range of pulsation is typically between 60 and 100 pulses (or beats) per minute. The light sensor 122 will produce a signal (that is passed to the controller 124) with a particular AC waveform that corresponds to the movement of the blood through the vessel. In particular, the AC waveform corresponds to the light absorbed or reflected by the pulsatile blood flow within the vessel. On the other hand, the DC component corresponds principally to light absorbed, reflected and/or scattered by the tissues, and thus the vessel may appear as a "shadow" or "dip" in the curve formed of the DC signals from each of the sensors in a sensor array.

According to such embodiments, the controller 124 is coupled to the light sensor 122, and may include a splitter 126 to separate the first pulsatile component from the second non-pulsatile component for each element of the light sensor array 122. The controller 124 may also include an analyzer 128 to determine the presence of and/or characteristic(s) of the vessel V within the region 102 proximate to the working end 104 of the surgical instrument 106 based (at least in part) on the pulsatile component. According to the embodiments described herein, the analyzer may make that determination by first detecting or differentiating regions of interest in the DC signals from the light sensors 120 of the system 100.

Before discussing the details of the determination of the regions of interest, further details of the system may be discussed with reference, for example, to the transmittance-based embodiment of FIGS. 1 and 2, the light emitter 120 may include one or more elements, as referenced above. According to an embodiment schematically illustrated in FIG. 2, the light sensor 122 may include a first light emitter 120-1, a second light emitter 120-2, and a third light emitter 120-3. All of the light emitters may be configured to emit light at a particular wavelength (e.g., 660 nm), or certain emitters may emit light at different wavelengths than other emitters. Each light emitter may be a light emitting diode, for example.

As to those embodiments wherein the light emitter 120 is in the form of an array including one or more light emitting diodes, as is illustrated in FIG. 2, the diodes may be arranged in the form of a one-dimensional, two-dimensional or three-dimensional array. An example of a one-dimensional array may include disposing the diodes along a line in a single plane, while an example of a two-dimensional array may include disposing the diodes in a plurality of rows and columns in a single plane. Further example of a two-dimensional array may include disposing the diodes along a line on or in a curved surface. A three-dimensional array may include diodes disposed in more than one plane, such as in a plurality of rows and columns on or in a curved surface.

The light sensor 122 also may include one or more elements. Again, according to the embodiment illustrated in FIG. 2, the light sensor 122 may include a first light sensor 122-1, a second light sensor 122-2, an n-th light sensor 122-$n$, and so on. As was the case with the light emitters 120-1, 120-2, 120-3, the light sensors 122-1, 122-2, 122-3, 122-$n$ may be arranged in an array, and the discussion about the arrays above applied with equal force here.

In fact, where the array of light sensors 122 includes a row of light sensors (such as in FIG. 2), the array 122 may be referred to in the alternative as a linear array. The individual light sensors of the array 122 may be disposed adjacent each other, or the light sensors may be spaced from each other. It may even be possible for the individual light sensors that define a row of light sensors to be separated from each other by light sensors that define a different row or column of the array. According to a particular embodiment, however, the array may comprise a charge coupled device (CCD), and in particular linear CCD imaging device comprising a plurality of pixels. As a further alternative, a CMOS sensor array may be used.

The system 100 may include hardware and software in addition to the emitter 120, sensor 122, and controller 124. For example, where more than one emitter 120 is used, a drive controller may be provided to control the switching of the individual emitter elements. In a similar fashion, a multiplexer may be provided where more than one sensor 122 is included, which multiplexer may be coupled to the sensors 122 and to an amplifier. Further, the controller 124 may include filters and analog-to-digital conversion as may be required.

According to certain embodiments, the splitter 126 and the analyzer 128 may be defined by one or more electrical circuit components. According to other embodiments, one or more processors (or simply, the processor) may be programmed to perform the actions of the splitter 126 and the analyzer 128. According to still further embodiments, the splitter 126 and the analyzer 128 may be defined in part by electrical circuit components and in part by a processor programmed to perform the actions of the splitter 126 and the analyzer 128.

For example, the splitter 126 may include or be defined by the processor programmed to separate the first pulsatile component from the second non-pulsatile component. Further, the analyzer 128 may include or be defined by the processor programmed to determine the presence of (or to quantify the size of, for example) the vessel V within the region 102 proximate to the working end 104 of the surgical instrument 106 based on the first pulsatile component. The instructions by which the processor is programmed may be stored on a memory associated with the processor, which memory may include one or more tangible non-transitory computer readable memories, having computer executable instructions stored thereon, which when executed by the processor, may cause the one or more processors to carry out one or more actions.

As to the operation of such a transmittance-based system to determine tissue and/or artifact (e.g., a vessel, such as a blood vessel or a ureter) characteristics, which characteristics may include position and dimension (e.g., length, width, diameter, etc.) by way of example and not by way of limitation, US Pub. Nos. 2015/0066000, 2017/0181701, 2018/0042522 and 2018/0098705 are each incorporated herein by reference in their entirety. As to associated structure and operation that may address issues related to the operation of such systems, PCT Application Nos. PCT/US16/55910, filed Oct. 7, 2016, and PCT/US17/48651, filed Aug. 25, 2017, are each incorporated herein by reference in their entirety.

Figure 5:
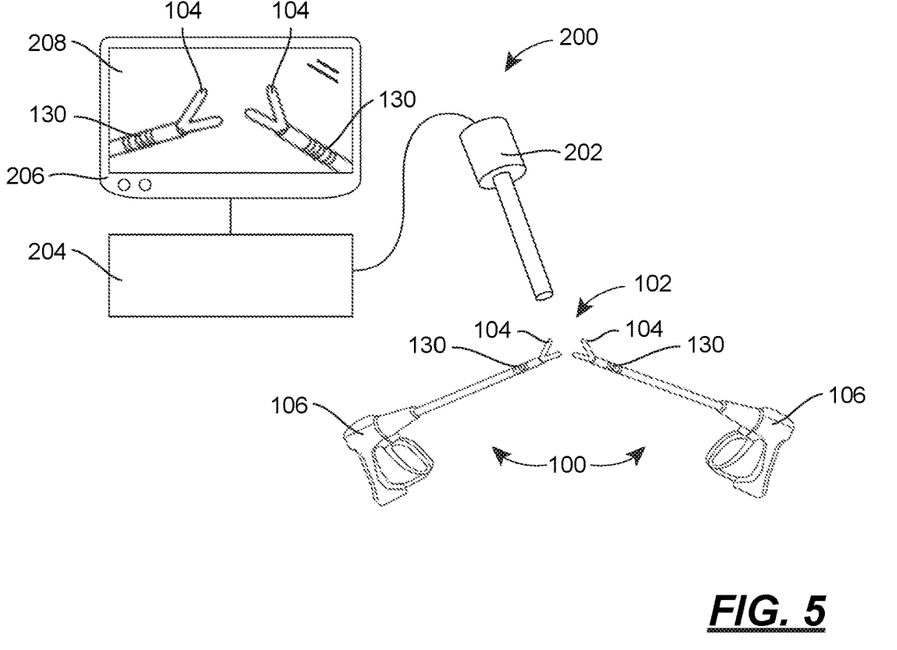
FIG. 5 is a schematic diagram of a surgical system according to an embodiment of the present disclosure, in combination with an embodiment of a video system, illustrating the surgical system in use with the video system.
Figure 6:
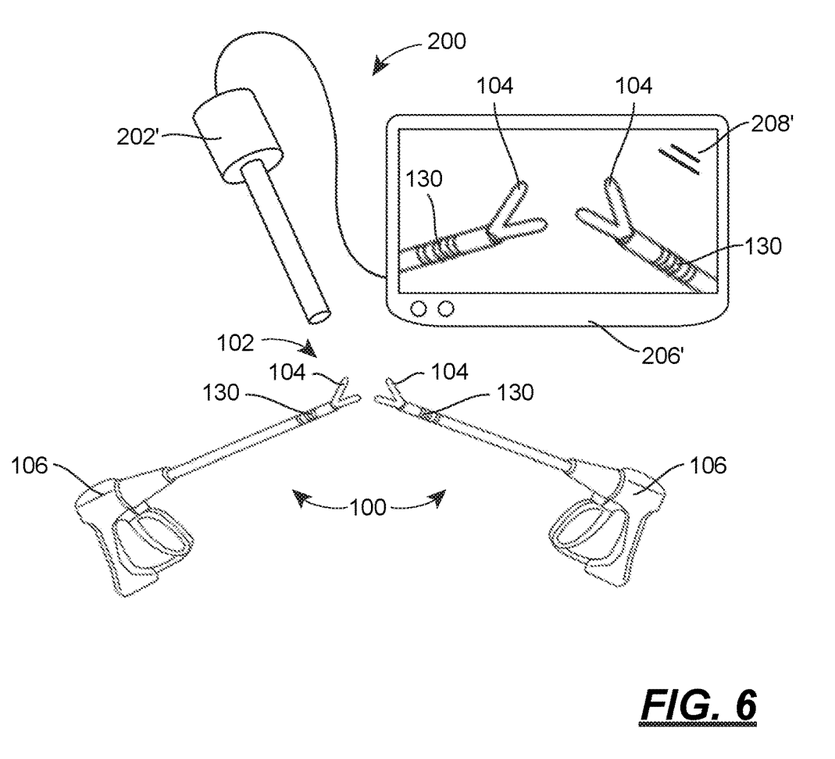
FIG. 6 is a schematic diagram of a surgical system according to an embodiment of the present disclosure, in combination with another embodiment of a video system, illustrating the surgical system in use with the video system.

FIGS. 5 and 6 illustrate an embodiment of the surgical system 100 in combination with embodiments of a video system 200, such as may be used conventionally during minimally invasive surgery or laparoscopic surgery, for example. The video system 200 includes a video camera or other image capture device 202, a video or other associated processor 204, and a display 206 having a viewing screen 208.

As illustrated, the video camera 202 is directed at the region 102 proximate the working ends 104 of two surgical instruments 106. As illustrated, both of the surgical instruments 106 are part of an embodiment of a surgical system 100, such as illustrated in FIG. 2 and discussed above. In this case, the instruments 106 each include a visual indicator 130. It will be recognized, however, that according to other embodiments only one of the instruments 106 may include a visual indicator 130. The other elements of the surgical system 100 are omitted for ease of illustration, although it will be noted that elements of the system 100, such as the splitter 126 and the analyzer 128, may be housed in the same physical housing as the video processor 204.

The signal from the video camera 202 is passed to the display 206 via the video processor 204, so that the surgeon or other member of the surgical team may view the region 102 as well as the working ends 104 of the surgical instruments 106, which are typically inside the patient. Because of the proximity of the visual indicators 130 to the working ends 104, and thus the region 102, the visual indicators 130 are also visible on the display screen 108. As mentioned previously, this advantageously permits the surgeon to receive visual cues or alarms via the visual indicators 130 via the same display 206 and on the same display screen 208 as the region 102 and the working ends 104. This, in turn, limits the need of the surgeon to look elsewhere for the information conveyed via the visual indicators 130.

FIG. 6 illustrates another embodiment of a video system 200 that can be used in conjunction with an embodiment of the surgical system 100. According to this embodiment, the video processor 204 is not disposed in a housing separate from the video camera 202', but is disposed in the same housing as the video camera 202'. According to a further embodiment, the video processor 204 may be disposed instead in the same housing as the remainder of the display 206' as the display screen 208'. Otherwise, the discussion above relative to the embodiment of the video system 200 illustrated in FIG. 5 applies equally to the embodiment of the video system 200 illustrated in FIG. 6.

Figure 1:
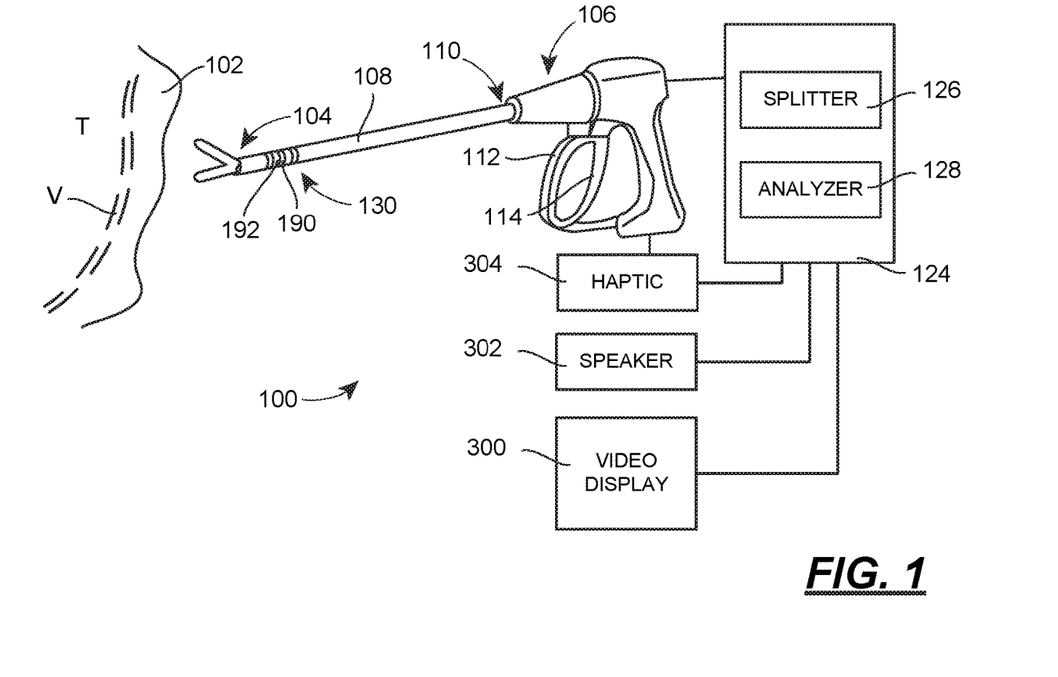
FIG. 1 is a schematic diagram of a surgical system according to an embodiment of the present disclosure.

While the user interface 130 advantageously permits the surgeon or surgical team to view an output from the controller 124, it is possible to include other output devices with the user interface 130, as illustrated in FIGS. 1 and 2. For example, an alert may be displayed on a video monitor 300 being used for the surgery (e.g., the display 206, 206' in FIGS. 5 and 6), or may cause an image on the monitor to change color or to flash, change size or otherwise change appearance. The auxiliary output may also be in the form of or include a speaker 302 that provides an auditory alarm. The auxiliary output also may be in the form of or may incorporate a safety lockout associated with the surgical instrument 106 that interrupts use of the instrument 106. For example, the lockout could prevent ligation or cauterization where the surgical instrument 106 is a thermal ligature device. As a still further example, the auxiliary output also may be in the form of a haptic feedback system, such as a vibrator 304, which may be attached to or formed integral with a handle or handpiece of the surgical instrument 106 to provide a tactile indication or alarm. In addition to the light emitting elements disposed at the working end 104 of the surgical instrument 108, one or more light emitting elements may be disposed at the proximal end 110 of the shaft 108, such as disposed on or attached to the grip or handle 112, to provide a visual indication or alarm. Various combinations of these particular forms of the auxiliary output may also be used.

As mentioned above, the surgical system 100 may also include the surgical instrument 106 with the working end 104, to which the user interface 130 and the sensor (and in preferred embodiments, the light emitter 120 and the light sensor 122) are attached (in the alternative, removably/reversibly or permanently/irreversibly). The user interface 130 and sensor may instead be formed integrally (i.e., as one piece) with the surgical instrument 106. As also stated, it is possible that the user interface 130 and sensor be attached to a separate instrument or tool that is used in conjunction with a surgical instrument or tool 106.

As noted above, the surgical instrument 106 may be a thermal ligature device in one embodiment. In another embodiment, the surgical instrument 106 may simply be a grasper or grasping forceps having opposing jaws. According to still further embodiments, the surgical instrument may be other surgical instruments such as irrigators, surgical staplers, clip appliers, and robotic surgical systems, for example. According to still other embodiments, the surgical instrument may have no other function that to carry the user interface and sensor and to place them within a surgical field. The illustration of a single embodiment is not intended to preclude the use of the system 100 with other surgical instruments or tools 106.

In the context of one or more of the systems described above, it will be recognized that preliminary to characterization of an artifact (e.g., determining a diameter for a vessel) from data received from an array of light sensors, identification of a region of interest is important. Further, it is advantageous that the identification of the region of interest be relatively robust relative to environmental factors that may influence the identification of a region of interest. In addition, it is advantageous that the identification of the region of interest minimize the computational burden of making the identification. In conjunction with the former, an identification system and method that minimizes the computational burden may also facilitate the use of the system and method in real time or near real time implementations.

As noted above, the systems 100 described include light emitters 120 and light sensors 122, and that the signal from the light sensors may include a pulsatile (or AC) component and a non-pulsatile (or DC) component. The system and method for identification of a region of interest described herein utilizes the non-pulsatile, or DC, component. This DC data may be described in terms of a DC curve that includes DC data from a plurality of light sensors arranged in a array, for example a linear array, according to at least one embodiment described herein.

Figure 7:
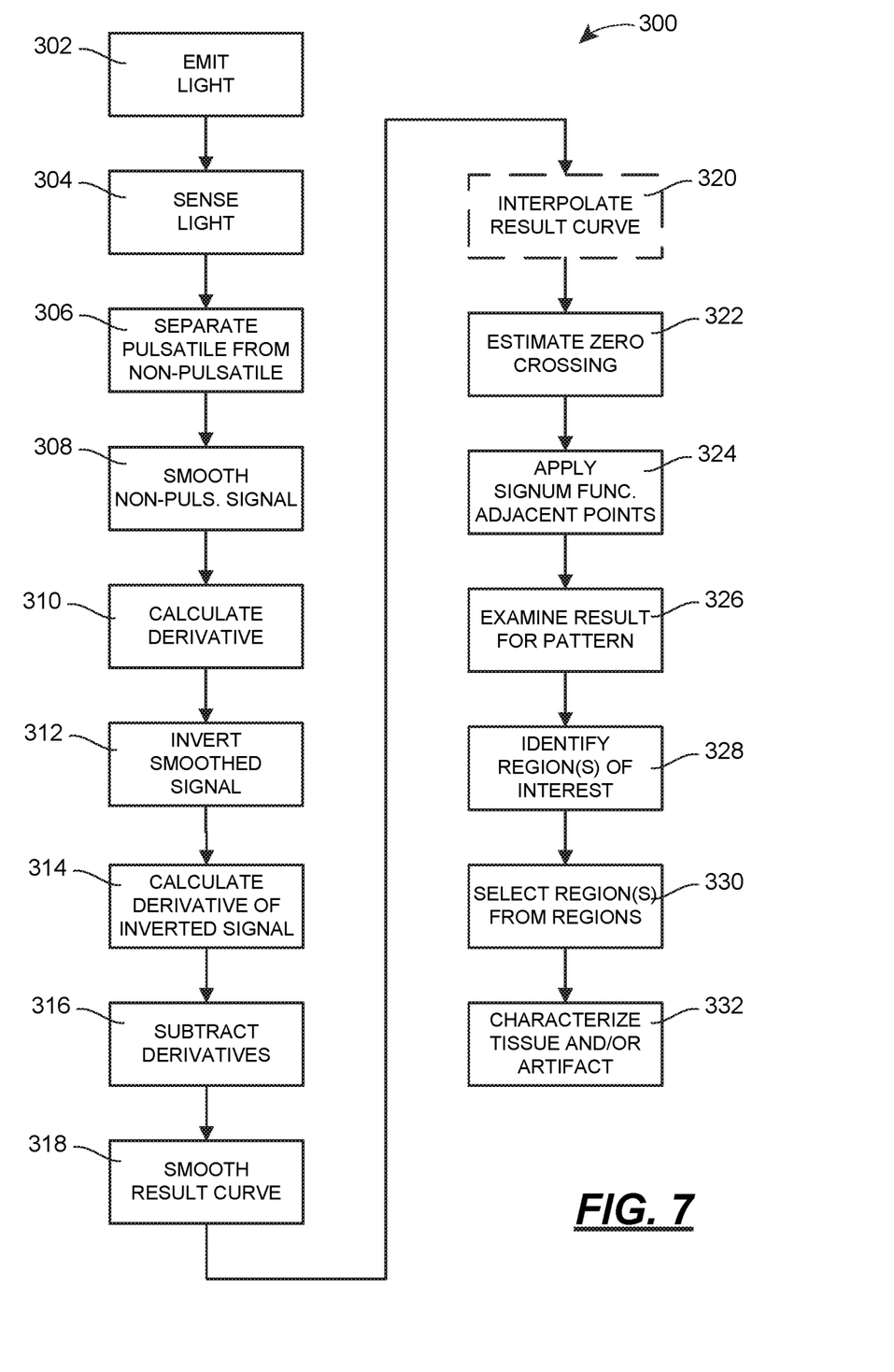
FIG. 7 is a flowchart of a method used by any of the foregoing systems to detect or differentiate one or more regions of interest within the signal(s) received from an array of light sensors, which detection or differentiation of one or more regions of interest leads to detection or differentiation of tissue or one or more artifacts.

In general terms, the method illustrated in FIG. 7 may be used to determine regions of interest where a "dip" occurs in the DC curve (i.e., a region along the DC curve where the profile decreases and then increases). According to certain embodiments, all dips may be identified as regions of interest. According to other embodiments, the regions of interest then may be processed further to determine which of the regions of interest have a high (or higher) probability of being associated with a particular artifact, such as a vessel, and, in particular, a blood vessel. For example, a region of interest that exhibits a high (or higher) probability of being associated with a blood vessel may be separated from regions of interest that are associated with heterogeneous or highly absorbing tissue. In this fashion, the method may be used to localize and track the blood vessel along the sensor array in real-time.

As described with reference to FIG. 7, a method 300 for identifying regions of interest is described, which may be used with the embodiments of the system 100 described above. The embodiment of the method 300 illustrated in FIG. 7 begins a block 302, where the system 100 controls the light emitters 120 to emit light of one or more wavelengths. The method 300 continues at block 304, where the light sensors 122 receive light and generate a signal according to the light detected. Presumably, a significant portion of the light received by the light sensors 122 is from the light emitters 120, but it will be recognized that ambient light (i.e., light from other sources) may also contribute to the light received by the light sensors 122. Further, in keeping with the discussion above, the light received by the light sensors 122 may include a pulsatile and a non-pulsatile component, in particular when the light is received after passing through tissue including a vessel, such as a blood vessel.

At block 306, the system 100 separates the signal(s) received from the light sensors 122 into pulsatile and non-pulsatile components. For example, the splitter 126 may be used to separate the different components of the signal(s). Further, it will be recognized that while the method 300 utilizes the non-pulsatile (or DC) component, the pulsatile (or AC) component may be utilized as well by the system 100 in a separate method, or in conjunction with the output of the method 300.

According to an embodiment of the method 300, the system 100 smoothes DC curve, which curve may include the DC signals corresponding to each of the light sensors 122 along the array. In this regard, smoothing may include filtering, which filtering may include averaging as well. The smoothing of the DC curve may assist in focusing on those sensors generating signals with the most pronounced DC signal relative to other sensors.

At block 310, the system 100 determines a derivative of the smoothed DC curve generated at block 308. In particular, the system 100 uses a 3-point numerical differentiation to determine the derivative, although other n-point numerical differentiations could be used instead. The system 100 uses a numerical differentiation to determine the derivative to reduce the computational burden presented by the method 300.

At block 312, the system 100 inverts the smoothed signal determined at block 308. At block 314, the system 100 determines a derivative of the inverted smoothed DC curve. As was the case with block 310, the system may determine the derivative by using a 3-point numerical differentiation, for example. Again, using a numerical differentiation may reduce the computational burden of the method 300.

At block 316, the system 100 subtracts the derivative determined at block 314 from the derivative determined at block 310. The system 100 then smoothes the result of this subtraction at block 316, referred to as the resultant curve, to generate a smoothed, resultant curve at block 318. The system 100 then optionally interpolates the smoothed resultant curve at block 320 for use in the remainder of the method 300; alternatively, the smoothed resultant curve can be used in the remainder of the method 300.

At block 322, the system 100 estimates the zero crossings of the smoothed (and optionally interpolated) resultant curve. The system 100 then applies a signum function to points adjacent the estimates zero crossings of the resultant curve at block 324, and determines if the result of applying the signum function for the points adjacent present a specific pattern at block 326. In particular, the system 100 may analyze the result for a pattern of [1, −1, 1], [1, −1], [−1, 1] for the points adjacent the zero crossing, suggesting a dip has occurred in the original signal curve. The system 100 then identifies this region as a region of interest at block 328.

As is reflected in FIG. 7, the system may identify more than one region of interest at block 328. That is, based on the number of zero crossings and the patterns established for the points adjacent those zero crossings, the system may identify no region of interest, one region of interest, or a plurality of regions of interest. In identifying a plurality of regions of interest, the determination at block 328 may be repeated or may occur multiple times.

As is further reflected in the method 300 of FIG. 7, in those circumstances where a plurality of regions of interest are determined at block 328, the system 100 may perform additional actions at block 330 to select one or more of the regions of interest from the plurality of regions determined at block 328. For example, in some embodiments, certain regions of interest may be selected relative to others based on the likelihood that a vessel is associated with the region; in other embodiments, all of the regions of interest may be considered, where attempting to identify different tissues, for example. The system 100 then will perform further analysis at block 332 on the one or more regions of interest, such as to determine the size (e.g., diameter or effective diameter) of the vessels associated with these regions of interest, for example according to the methods disclosed in the references incorporated by reference in their entirety herein.

Figure 8:
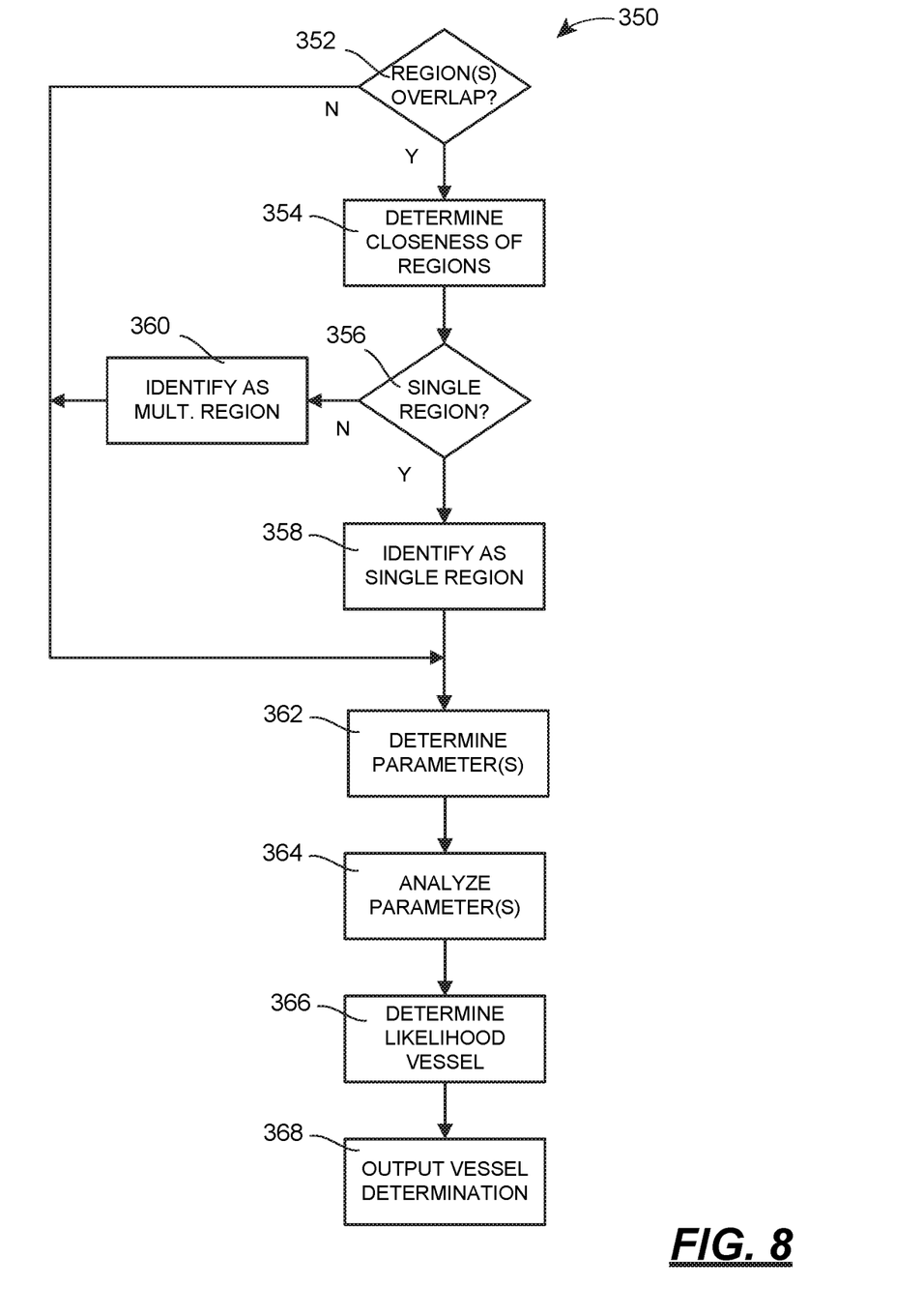
FIG. 8 is a flowchart of a method used by any of the foregoing systems to select those regions of interest from among a plurality of regions of interest that are more or less likely to be associated with, for example, an artifact such as a vessel.

As one example of the actions that may be performed to select one or more regions of interest from a plurality of identified regions of interest, a method 350 is illustrated in FIG. 8, which method may be used to determine which regions of interest among a plurality of regions of interest may be more or less likely to have a vessel (e.g., a blood vessel, such as to have an artery or vein) associated therewith. In general terms, the method 350 first determines which regions of interest may overlap, and resolves whether the overlapping regions of interest should be treated as a single region of interest or as separate regions of interest. Having resolved the overlap issue, the method 350 then seeks to determine if each of the remaining regions of interest is more or less likely to be associated with a vessel. As noted above, it is possible that after performing the method 350, multiple regions are identified as regions of interest for possible further processing.

The method 350 begins at block 352 where a determination is made whether any of the regions of interest overlap. This determination may be made whether a starting point of a region of interest lies between the starting and ending points of another region of interest and/or whether an ending point or a region of interest lies between the starting and ending points of another region of interest. The starting and ending points of a region of interest may be determined by comparing the results of the signum function, as explained above. If there are regions of interest that overlap, the method 350 continues to block 354; if there are no regions of interest that overlap, the method 350 continues to block 362.

Assuming that it is determined that at least two regions of interest overlap at block 352, an analysis of the closeness of the regions of interest is performed at block 354. In general terms, if the regions of interest are sufficiently close, such that it is unlikely that any two vessels would actually be that close in reality, the system 100 may treat the regions of interest as a single region of interest; otherwise, the regions may be treated as separate regions. According to one embodiment, the closeness determination may include a determination of 1) the closeness between ending points of adjacent regions; 2) the closeness of the starting point of one region and the ending point of the previous region; and 3) the closeness between starting points of adjacent regions. That is, where D is $$\begin{bmatrix} d_{11} & d_{12} \\ \vdots & \vdots \\ d_{n1} & d_{n2} \end{bmatrix}$$

with the first element in each column being the starting point and the second element in each column being the ending point, the above closeness determinations (or factors) may be expressed as the following:

$|D[2:n,2]-D[1:n-1,2]|$ $D[2:n,1]-D[1:n-1,2]$ $|D[2:n,1]-D[1:n-1,1]|$

Based on the results of the analysis at block 354, the method 350 may determine whether to identify the regions as a single region at 356, and either identify multiple regions (e.g., two regions) as a single region at block 358 or identify the regions as separate regions at block 360.

Having resolved the overlapping region issues, the method 350 continues with the determination of which of the remaining regions is more or less likely to be associated with an artifact, e.g., a vessel. The determination could answer either or both of these questions (i.e., more or less likely), but the purpose is to identify the more likely regions of interest for further processing. While the method 350 of FIG. 8 includes one embodiment for making this determination, other embodiments are possible for also making this determination.

According to the method 350, a plurality of parameters is analyzed at block 362 to determine if each of the regions of interest is more likely (or less likely) to be associated with a vessel. Each of the parameters may be analyzed at block 364 to determine if the parameter is satisfied, or is not, by comparing the parameter against a threshold associated with the parameter, for example. After each of the parameters is compared against its respective threshold, the results of all of the comparisons may be analyzed at block 366 to determine if it is more likely that a vessel is present, for example by comparing the analysis performed at block 364 against a further criterion. The determination(s) made at block 366 is/are then provided as an output at block 368, for example for purposes of identifying regions of interest for further processing as part of the method 300 of FIG. 7. It will be recognized that the actions of blocks 362, 364, 366, 368 may be repeated as necessary to address all of the regions of interest identified.

In the embodiment of FIG. 8, the following five parameters are considered: 1) width, 2) the standard deviation of the derivative of the region of interest, 3) the mean of the derivative of the individual values of the sensors associated with the region of interest/the standard deviation of the derivative of the individual values of the sensors associated with the region of interest, 4) the minimum value from among the individual values of the sensors associated with the region of interest, and 5) the standard deviation to the individual values of the sensors associated with the region of interest/the mean of the individual values. According to other embodiments, other parameters may be considered, and the total number of parameters may be more or less than five. These parameters may be determined at block 362 in a particular order, or may be determined simultaneously or near simultaneously. The method 350 may determine each parameter separately and proceed immediately to the analysis of the parameter at block 364, or may determine all parameters (whether sequentially or simultaneously/near simultaneously) at block 362 and then proceed to block 364.

At block 364, the parameters determined at block 362 are analyzed to determine if the parameter indicates that it is more or less likely that a vessel is associated with the region of interest. For example, the width parameter may be compare with a minimum width, the minimum width representing an actual limit on the size of the vessels expected or of the vessels of interest. As noted above, the use of a threshold comparison is not the only analysis method that may be used to determine if the parameters are more or less suggestive of a vessel being present in the region of interest.

At block 366, a determination is made based on the analysis at block 364 of each of the parameters determined at block 362 whether a vessel is more or less likely to be associated with a region of interest. For example, according to the present embodiment, the determination whether it is more likely that a vessel is present requires the satisfaction of all of the parameters. According to other embodiments, it may be sufficient that a simple majority of the parameters are in excess of the associated thresholds, for example. Still other embodiments may use a weighted average of the results from the parameter comparisons. In any event, after the determination is made at block 366, the results are provided at block 368.

After the system 100 has determined which regions of interest to evaluate, such as using a method such as is illustrated in FIG. 8, the system 100 may characterize the artifact at block 332 of FIG. 7. For example, the characterization occurring at block 332 may include determining if the artifact is a vessel, and if so, if the vessel is a particular type of vessel (e.g., an artery). Alternatively, the characterization occurring at block 332 may be between different types of tissue. As a further alternative, the characterization may include determining a dimension of the artifact: for example, where the artifact is a vessel, the dimension may be a diameter (where the vessel is considered or assumed to be circular in cross-section) or effective diameter (where the vessel is considered or assumed to be other than circular in cross-section, but the largest dimension across the vessel may be used in lieu of an actual diameter).

In this regard, the action or actions carried out by the system 100 at block 332 to determine tissue and/or artifact (e.g., a vessel, such as a blood vessel or a ureter) characteristics, which characteristics may include position and dimension (e.g., length, width, diameter, etc.), may include by way of example and not by way of limitation, for a transmittance-based system, those described in US Pub. Nos. 2015/0066000, 2017/0181701, 2018/0042522 and 2018/0098705, each of which is incorporated herein by reference in their entirety.

In conclusion, although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention since describing every possible embodiment would be impractical, if not impossible. Numerous alternative embodiments could be implemented, using either current technology or technology developed after the filing date of this patent, which would still fall within the scope of the claims defining the invention.

It should also be understood that, unless a term is expressly defined in this patent using the sentence "As used herein, the term '______' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112(f).

What is claimed is:

1. A surgical system including a surgical instrument, the surgical system comprising:
   at least one light emitter disposed at a working end of the surgical instrument;
   an array of light sensors disposed at the working end of the surgical instrument, individual light sensors in the array of light sensors adapted to generate a signal comprising a non-pulsatile component; and
   a controller coupled to the array of light sensors, the controller comprising an analyzer configured to:
      determine a curve of the non-pulsatile components of the signals of each of the individual light sensors in the array of light sensors,
      smooth the curve to generate a smoothed curve;
      calculate a derivative of the smoothed curve;
      invert the smoothed curve to generate an inverted smoothed curve;
      calculate a derivative of the inverted smoothed curve;
      take a difference between the derivative of the inverted smoothed curve and the derivative of the smoothed curve to generate a resultant curve;
      smooth the resultant curve to generate a smoothed, resultant curve;
      estimate zero crossings of the smoothed, resultant curve;
      apply a signum function to points adjacent each zero crossing, if any, to generate a result; and
      identify a region of interest, if any, based on the result for points adjacent each zero crossing, if any.

2. The surgical system according to claim 1, wherein the analyzer is configured to calculate a 3-point differentiation of the smoothed curve to calculate the derivative of the smoothed curve.

3. The surgical system according to claim 1, wherein the analyzer is configured to calculate a 3-point differentiation of the inverted smoothed curve to calculate the derivative of the inverted smoothed curve.

4. The surgical system according to claim 1, wherein the analyzer is configured to interpolate the smoothed, resultant curve before estimating zero crossings of the smoothed, resultant curve.

5. The surgical system according to claim 1, wherein the analyzer is configured to identify a plurality of regions of interest based on the result for points adjacent each zero crossing, to identify a region from the plurality of regions of interest, and to characterize an artifact associated with the region.

6. The surgical system according to claim 1, wherein the controller comprises a processor and memory, the analyzer comprising the processor programmed to determine a curve of the non-pulsatile components of the signals of each of the individual light sensors in the array of light sensors, to smooth the curve to generate a smoothed curve, to calculate a derivative of the smoothed curve, to invert the smoothed curve to generate an inverted smoothed curve, to calculate a derivative of the inverted smoothed curve, to take a difference between the derivative of the inverted smoothed curve and the derivative of the smoothed curve to generate a resultant curve, to smooth the resultant curve to generate a smoothed, resultant curve, to estimate zero crossings of the smoothed, resultant curve, to apply a signum function to points adjacent each zero crossing, if any, to generate a result, and to identify a region of interest, if any, based on the result for points adjacent each zero crossing, if any.

7. The surgical system according to claim 1, wherein the analyzer is configured to characterize an artifact based on the region of interest identified.

8. The surgical system according to claim 7, wherein the analyzer is configured to determine a diameter or an effective diameter of a vessel based on the region of interest identified.

* * * * *